US008673841B2

United States Patent
Alagarsamy et al.

(10) Patent No.: US 8,673,841 B2
(45) Date of Patent: Mar. 18, 2014

(54) OXYTOCIN ANALOGUES

(75) Inventors: Sudar Alagarsamy, San Diego, CA (US); Robert Galyean, Escondido, CA (US); Kaszimierz Wisniewski, San Diego, CA (US); Claudio Schteingart, San Diego, CA (US)

(73) Assignee: Ferring B.V., Hoofdorp (NL)

( * ) Notice: Subject to any disclaimer, the term of this patent is extended or adjusted under 35 U.S.C. 154(b) by 329 days.

(21) Appl. No.: 12/933,858

(22) PCT Filed: Mar. 30, 2009

(86) PCT No.: PCT/IB2009/005351
§ 371 (c)(1),
(2), (4) Date: Nov. 4, 2010

(87) PCT Pub. No.: WO2009/122285
PCT Pub. Date: Oct. 8, 2009

(65) Prior Publication Data
US 2011/0044905 A1 Feb. 24, 2011

Related U.S. Application Data

(60) Provisional application No. 61/040,973, filed on Mar. 31, 2008.

(30) Foreign Application Priority Data

May 19, 2008 (EP) .................................... 08251739

(51) Int. Cl.
*A61K 38/00* (2006.01)
(52) U.S. Cl.
USPC ......... 514/1.1; 424/1.11; 424/1.65; 424/1.69; 424/9.1; 530/300
(58) Field of Classification Search
USPC .......... 424/1.11, 1.65, 1.69, 9.1, 9.2, 9.3, 9.4, 424/9.5, 9.6, 9.7, 9.8; 514/1, 1.1; 534/7, 534/10–16; 530/300, 315, 317, 328, 329, 530/330
See application file for complete search history.

(56) References Cited

FOREIGN PATENT DOCUMENTS

WO 03072597 9/2003

OTHER PUBLICATIONS

Meisenberg G et al., "Behavioral Effects of Intra Cerebro Ventricularly Administered Neuro Hypophyseal Hormone Analogs in Mice," Pharmacology Biochemistry and Behavior 16(5):819-826 (1982).
Grzonka Z et al., Synthesis and some Pharmacological Properties of Oxytocin and Vasopressin Analogs with Sarcosine or N Methyl-L Alanine in Position 7, Journal of Medicinal Chemistry 26(4):555-559 (1983).
Grzonka et al., "Synthesis and Some Pharmacological Properties of [4-Threonine,7-sarcosine]oxytocin, a Peptide with High Oxytocic Potency, and of [4-Threonine,7-N-methylalanine]oxytocin"; Journal of Medicinal Chemistry; vol. 26; No. 12; pp. 1786-1787 (1983).
European Examination Report mailed Feb. 17, 2011 n corresponding EP Application No. 09 727 031.8.
European Examination Report mailed Mar. 11, 2013 in corresponding EP Application No. 09 727 031.8.
International Preliminary Report on Patentability issued Oct. 5, 2010 in corresponding International Application No. PCT/IB2009/005351.
Response to examination report in corresponding EP Application No. 09727031.8, filed May 24, 2013.
Response to examination report in corresponding EP Application No. 09727031.8, filed Jun. 14, 2011.
Supplemental response to examination report in corresponding EP Application No. 09727031.8, filed Feb. 11, 2013.

*Primary Examiner* — D L Jones
(74) *Attorney, Agent, or Firm* — Fish & Richardson P.C.

(57) ABSTRACT

The present invention relates to novel compounds, pharmaceutical compositions comprising the same, use of said compounds for the manufacture of a medicament for treatment of inter alia compromised lactation conditions as well as to a method for treatment of said conditions, wherein said compounds are administered. The compounds are represented by the general formula (I), as further defined in the specification.

(I)

22 Claims, No Drawings

OXYTOCIN ANALOGUES

CROSS REFERENCE TO RELATED APPLICATIONS

This application is a national phase filing under 35 U.S.C. §371 of International application number PCT/IB2009/005351, filed Mar. 30, 2009, which claims priority from provisional application No. 61/040,973 filed Mar. 31, 2008 and EP application number 08251739.2 filed May 19, 2008. The International Application published in English on Oct. 8, 2009 as WO 2009/122285 under PCT Article 21(2). The entire content of the prior applications are incorporated herein by reference in their entirety.

FIELD OF THE INVENTION

The present invention relates to novel compounds, pharmaceutical compositions comprising the same, use of said compounds for the manufacture of a medicament for treatment of inter alia compromised lactation conditions as well as to a method for treatment of said conditions, wherein said compounds are administered.

BACKGROUND

Peptidic oxytocin receptor agonists include the natural hormone oxytocin, and carbetocin.

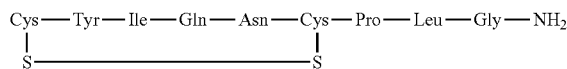

(oxytocin)

Oxytocin is a potent uterotonic agent, clinically used to induce labour, and has been shown to enhance the onset and maintenance of lactation, Gimpl, G. et al., *Physiol. Rev.* 81 (2001) 629-683 and Ruis H. et al., *British Medical Journal* 283 (1981) 340-342. Carbetocin (1-deamino-1-carba-2-tyrosine(O-methyl)-oxytocin) is also a potent uterotonic agent clinically used for the control of uterine atony and excessive bleeding. Further research indicates that oxytocin agonists are useful for the treatment of inflammation and pain, including abdominal and back pain; sexual dysfunction, both male and female; irritable bowel syndrome (IBS), constipation and gastrointestinal obstruction; autism, stress, anxiety (including anxiety disorder) and depression (Pitman R. et al., *Psychiatry Research*, 48:107-117; Kirsch P et al., *The Journal of Neuroscience*, 25(49):11489-11493); surgical blood loss, the control of post-partum haemorrhage, wound healing and infection; mastitis and placenta delivery; and osteoporosis. Additionally, oxytocin agonists may be useful for the diagnosis of both cancer and placental insufficiency.

A disadvantage of both oxytocin and carbetocin are their lack of selectivity over the vasopressin receptors, especially the $V_2$ receptor. During administration of oxytocin this disadvantage is observed by such side effects as antidiuresis and hyponatremia.

In order to improve the pharmacological properties of oxytocin, analogues of oxytocin have been synthesised. Such analogues are described by Grozonka Z. et al. in *J. Med. Chem.* 26 (1983) 555-559 and *J. Med. Chem.* 26 (1983) 1786-1787, and by Engstrøm T. et al. in *E. J. Pharmacol.* 355 (1998) 203-210. Additionally, oxytocin analogues with antagonist activity at the oxytocin receptor have been described by Fragiadaki M. et al. in *E. J. Med. Chem.* (2007) 799-806.

The present invention may provide selective, efficacious compounds, providing feasible alternatives and/or improvements e.g. in the treatment of compromised lactation conditions.

DISCLOSURE OF THE INVENTION

The present invention relates to compounds represented by the general formula (I):

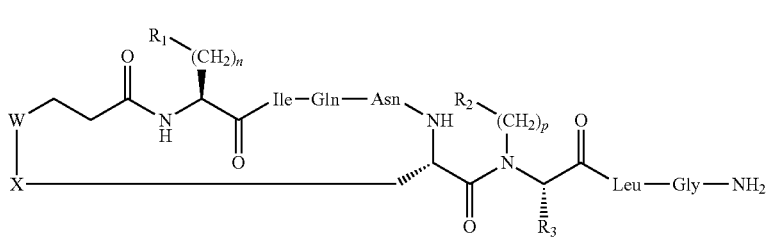

(I)

wherein:
n is selected from 0, 1 and 2;
p is selected from 0, 1, 2, 3, 4, 5 and 6;
$R_1$ is selected from aryl optionally substituted with at least one OH, F, Cl, Br, alkyl or O-alkyl substituent;
$R_2$ is selected from $R_4$, H, alkyl, cycloalkyl, aryl and 5- and 6-membered heteroaromatic ring systems;
$R_3$ is selected from H and a covalent bond to $R_2$, when $R_2$ is $R_4$, to form a ring structure;
$R_4$ is $C_{1-6}$ alkylene moiety substituted with at least one O-alkyl, S-alkyl or OH substituent;
W and X are each independently selected from $CH_2$ and S, but may not both be $CH_2$;
alkyl is selected from $C_{1-6}$ straight and $C_{4-8}$ branched chain alkyl and optionally has at least one hydroxyl substituent;
aryl is selected from phenyl and mono- or poly-substituted phenyl;
with the proviso that when $R_2$ is H, p is 1, $R_3$ is H, n is 1 and W and X are both S, $R_1$ is not 4-hydroxyphenyl;
cycloalkyl is selected from $C_{3-6}$ cycloalkyl and optionally has at least one hydroxyl substituent; and
solvates and pharmaceutically acceptable salts thereof.
The present invention may further relate to compounds represented by formula (I) above with the further proviso that when $R_2$ is H, p is 0, $R_3$ is H, n is 1 and W and X are both S, $R_1$ is not 4-hydroxyphenyl. Thus, the present invention may relate to compounds of formula (I) above with the proviso that the compound is not [1-β-Mpa, 7-Sar]OT and/or not {deamino[7-glycine]oxytocin}.

For the purposes of the present invention, the following terminology is used.

$C_{1-6}$ straight chain alkyl denotes having from one to six carbon atoms, including any number therebetween.

$C_{4-8}$ branched chain alkyl denotes all branched alkyl groups containing four to eight carbon atoms, including iso-, sec-, and tert-configurations, as said expression is not related to the binding site of the alkyl chain in question.

$C_{3-6}$ cycloalkyl denotes a carbocyclic ring system containing from three to six carbon atoms, including any number therebetween. The ring system may contain unsaturated bonds between carbon atoms.

A five-membered heteroaromatic ring system is a monocyclic aromatic ring system having five ring atoms, wherein 1, 2, 3 or 4 ring atoms are independently selected from N, O and S. Preferred ring systems are selected from a group consisting of thienyl, furyl, imidazolyl, thiazolyl, thiadiazolyl and tetrazolyl.

A six-membered heteroaromatic ring system is a monocyclic aromatic ring system having six ring atoms, wherein 1, 2, 3 or 4 ring atoms are independently selected from N, O and S. Preferred ring systems are selected from a group consisting of pyridyl.

Aryl denotes an aromatic group selected from phenyl and mono- or polysubstituted phenyl.

Substituent moieties may be selected from fluorine (F), chlorine (Cl) and bromine (Br) atoms and alkyl, hydroxy (—OH), alkoxy (—O-alkyl) and alkylthio (—S-alkyl).

Examples of pharmaceutically acceptable salts comprise acid addition salts, e.g. a salt formed by reaction with hydrohalogen acids such as hydrochloric acid and mineral acids, such as sulphuric acid, phosphoric acid and nitric acid, as well as aliphatic, alicyclic, aromatic or heterocyclic sulphonic or carboxylic acids such as formic acid, acetic acid, propionic acid, succinic acid, glycolic acid, lactic acid, malic acid, tartaric acid, citric acid, benzoic acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halobenzenesulphonic acid, trifluoroacetic acid, trifluoromethanesulphonic acid, toluenesulphonic acid and naphthalenesulphonic acid.

In preferred embodiments n is 1.

In preferred embodiments p is selected from 1, 2, 3, 4 and 5.

In preferred embodiments $R^1$ is selected from phenyl, 4-hydroxyphenyl, 4-methoxyphenyl and 4-ethylphenyl.

In preferred embodiments $R^2$ is selected from ethyl, n-propyl, n-butyl, cyclopropyl, 2-hydroxyethyl, 2-methoxyethyl, 2-phenylethyl, phenyl, benzyl, 2-methylphenyl, 3-methylphenyl, 4-methylphenyl, 4-methoxyphenyl, 4-fluorophenyl, 3,4-difluorophenyl, 2-thienyl, 2-tetrahydrofuryl, 2-furyl, 2-pyridyl and 4-pyridyl.

In preferred embodiments $R^3$ is H.

In preferred embodiments said ring structure is selected from (R)-4-methoxypyrrolidinyl, (R)-4-methylthiopyrrolidinyl and (S)-4-hydroxypyrrolidinyl.

In preferred embodiments W is $CH_2$ and X is S.

In preferred embodiments W is S and X is $CH_2$.

In preferred embodiments W and X are both S.

In the most preferred embodiment, the invention is a compound selected from a group consisting of:

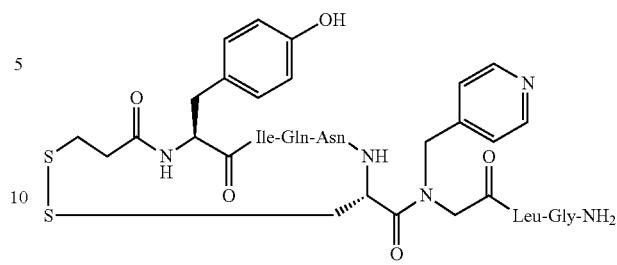

(10)

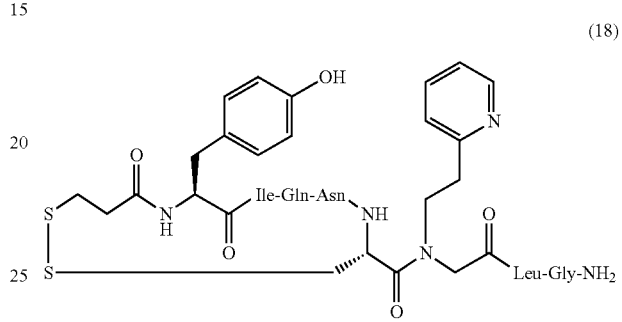

(18)

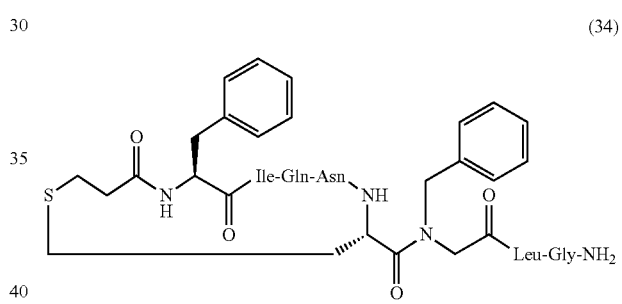

(34)

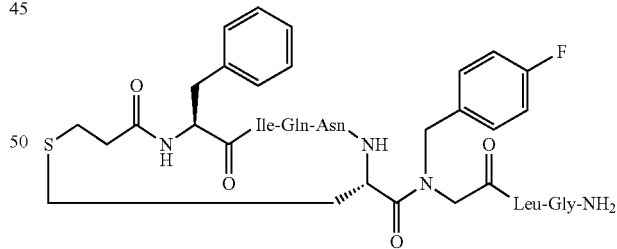

(47)

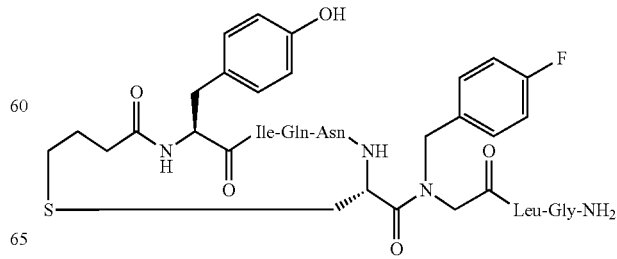

(49)

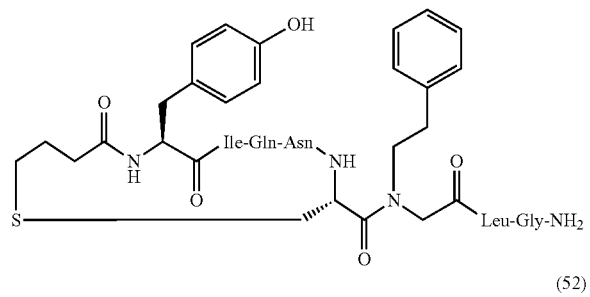

(51)

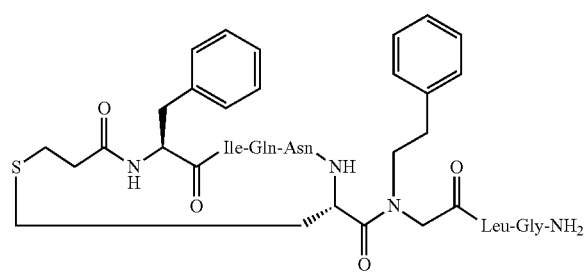

(52)

Furthermore the present invention relates to a compound as set forth above for the use as a pharmaceutical.

Accordingly, the present invention also relates to a pharmaceutical composition comprising a compound as set forth above as active ingredient in association with a pharmaceutically acceptable adjuvant, diluent or carrier.

The pharmaceutical composition may be adapted for oral, intravenous, topical, interperitoneal, nasal, buccal, intraocular, intra-aural, sublingual or subcutaneous administration or for administration via the respiratory tract e.g. in the form of an aerosol or an air-suspended fine powder. The composition may thus for instance be in the form of tablets, capsules, powders, microparticles, granules, syrups, suspensions, solutions, transdermal patches or suppositories.

It should be noted that the composition according to the present invention may optionally include two or more of the above outlined compounds.

The present pharmaceutical composition may optionally comprise e.g. at least one further additive selected from a disintegrating agent, binder, lubricant, flavouring agent, preservative, colourant and any mixture thereof. Examples of such and other additives are found in 'Handbook of Pharmaceutical Excipients'; Ed. A. H. Kibbe, 3$^{rd}$ Ed., American Pharmaceutical Association, USA and Pharmaceutical Press UK, 2000.

The present pharmaceutical composition may be adapted for nasal administration. It may comprise a sterile aqueous preparation of the compounds of the invention preferably isotonic with the blood of the recipient. This aqueous preparation may be formulated according to known methods using suitable dispersing or wetting agents and suspending agents. The nasal spray formulation SYNTOCINON® (oxytocin) is exemplary of a suitable pharmaceutical formulation applicable also for the inventive compounds disclosed herein. Water, Ringer's solution, and isotonic sodium chloride solution are exemplary acceptable diluents. The preparation may also include excipients such as sodium phosphate, citric acid, sodium chloride, glycerine, sorbitol solution, methylparaben, propylparaben and chlorobutanol.

In addition, the present invention relates to use of a compound as outlined above for, or for the manufacture of a medicament for, treatment of one or more medical conditions such as compromised lactation conditions; labour induction impairment; uterine atony conditions; excessive bleeding; inflammation and pain, including abdominal and back pain; sexual dysfunction, both male and female; irritable bowel syndrome (IBS), constipation and gastrointestinal obstruction; autism, stress, anxiety (including anxiety disorder) and depression; surgical blood loss, post-partum haemorrhage, wound healing and infection; mastitis and placenta delivery impairment; and osteoporosis; and for the diagnosis of cancer and placental insufficiency. Herein, the term anxiety includes anxiety disorder. Anxiety disorder includes the sub indications generalized anxiety disorder, panic disorder, agoraphobia, phobias, social anxiety disorder, obsessive-compulsive disorder, post-traumatic stress disorder, and separation anxiety.

In another embodiment the invention relates to a method for treatment of compromised lactation conditions; labour induction impairment; uterine atony conditions; excessive bleeding; inflammation and pain, including abdominal and back pain; sexual dysfunction, both male and female; irritable bowel syndrome (IBS), constipation and gastrointestinal obstruction; autism, stress, anxiety (including anxiety disorder) and depression; surgical blood loss, post-partum haemorrhage, wound healing and infection; mastitis and placenta delivery impairment; and osteoporosis; and for the diagnosis of cancer and placental insufficiency.

The typical dosage of the compounds according to the present invention varies within a wide range and will depend on various factors such as the individual needs of each patient and the route of administration. A physician of ordinary skill in the art will be able to optimise the dosage to the situation at hand.

For example, if the composition of the invention is for enhancing the onset and maintenance of lactation, (for example, for intranasal administration), a typical dose may be in the range of 0.05 to 1.0 µg/kg body weight for every breast pumping session. An intranasal dose may be divided into, for example, 1, 2, or 3 sub-doses (e.g. puffs), for example delivered to one or both nostrils as needed. The skilled person or physician may consider relevant variations to this dosage range and practical implementations to accommodate the situation at hand.

In a further example, the composition of the invention may be administered as an intravenous (iv) infusion, for example, for the treatment of postpartum haemorrhage or surgical blood loss. In this example it may be administered over a longer period. An example dosage for administration by intravenous infusion is 0.5-200 µg/kg body weight per hour.

In a further example, the composition of the invention may be for subcutaneous (sc), intranasal, or buccal administration, for example to treat anxiety disorder or depression. An example dosage for subcutaneous (sc), intranasal, or buccal administration is 0.5-1000 µg/kg body weight. The dosage may be, for example, for administration as many times a day as needed, for example, once or twice a day.

The abbreviations used are:
AcOH acetic acid
Boc tert-butoxycarbonyl
BOP benzotriazol-1-yloxy trisdimethylaminophosphonium hexafluorophosphate
Bua butyric acid
Bu butyl-alkyl residues may be further denoted a n (normal, i.e. unbranched), i (iso), s (sec and t (tertiary)
$CH_3CN$ Acetonitrile
DCC N,N'-dicyclohexylcarbodiimide
DCM dichloromethane DIC N,N'-diisopropylcarbodiimide
DIPEA N,N-diisopropylethylamine
DMF N,N-dimethylformamide
4-FBzlGly N-(4-fluorobenzyl)glycine
Fmoc 9-fluorenylmethoxycarbonyl
Fmoc-Cl 9-fluorenylmethoxycarbonyl chloride
Fmoc-OSu N-(9-fluorenylmethoxycarbonyl) succinimide
h hour(s)
HBTU O-(benzotriazol-1-yl)-N,N,N',N'-tetramethyluronium hexafluorophosphate
Hcy Homocysteine
HF hydrogen fluoride
HOBt 1-hydroxybenzotriazole
HPLC high performance liquid chromatography
IPA isopropylalcohol
MeOH Methanol
MBHA 4-methylbenzyhydrylamine
NMM 4-methylmorpholine
4-Pic 4-picolyl (4-pyridylmethyl)
PyBOP benzotriazol-1-yloxy trispyrrolidinephosphonite hexafluorophosphate
tBu tert-butyl
tBuOH tert-butylalcohol
TEA triethylamine
TFA trifluoroacetic acid
TIS triisopropylsilane
Trt trityl[triphenylmethyl, $(C_6H_5)_3C-$]

Unless otherwise specified L-amino acids were used and conventional amino acid terminology is adhered to.

EXPERIMENTAL

Synthesis

Amino acid derivatives and resins were purchased from commercial providers (Bachem, Novabiochem and Peptides International). N-Fmoc-N—$(R_2(CH_2)_p)$glycine, Fmoc-Cys (t-butoxycarbonylpropyl)-OH and Fmoc-Hcy(t-butoxycarbonylethyl)-OH were synthesised according to literature [Weber et al., *J. Med. Chem.*, 46 1918 (2003), Prochazka et al. *Collect. Czech. Chem. Commun.*, 57, 1335 (1992) and Wisniewski et al. in WO 03/072597]. Other chemicals and solvents were provided from Sigma-Aldrich, Fluka and Acros Organics.

The compounds herein were synthesised by standard methods in solid phase peptide chemistry utilising both Fmoc and Boc methodology. All coupling of Fmoc-protected amino acids were mediated with DIC/HOBt/DMF and all coupling of Boc-protected amino acids were mediated with DIC or DCC in DCM. Removal of the Fmoc group was performed with 20% piperidine in DMF and removal of the Boc group was performed in 50% TFA/DCM with 1% m-cresol for 5 and 25 minutes. Requisite resin washings were performed with DCM, IPA, DMF, and MeOH. Neutralization, as necessary, was accomplished with 2 resin washes of 10% TEA/DCM for 5 minutes.

Unless otherwise provided, all reactions were performed at room temperature. In addition to the references cited supra, the following standard reference literature provides further guidance on general experimental set up, as well as on the availability of required starting material and reagents:

Kates, S. A., Albericio, F., Eds., *Solid Phase Synthesis: A Practical Guide*, Marcel Dekker, New York, Basel, 2000;

Stewart, J. M., Young, J. D., *Solid Phase Synthesis*, Pierce Chemical Company, 1984;

Bisello, et al., *J. Biol. Chem.* 1998, 273, 22498-22505; and

Merrifield, *J. Am. Chem. Soc.* 1963, 85, 2149-2154.

Purity of the synthesised peptide may be determined by analytical reverse phase HPLC. Structural integrity of the peptides may be confirmed using amino acid analysis and electrospray mass spectrometry.

Fmoc and Boc methodologies were used to synthesise the resin bound 8 position (Leu) and 9 position (Gly) dipeptide.

The amino acid derivative in the 7 position of the amino acid residue was introduced via one of two routes: either bromoacetic acid was coupled to the resin bound dipeptide under DIC/HOBt/DMF conditions and the bromine atom was displaced with $(R_2(CH_2)_p)NH_2$ providing a resin-bound N—$(R_2(CH_2)_p)$glycine; or N-Fmoc-N—$(R_2(CH_2)_p)$glycine or an Fmoc-pro-OH derivative was coupled to the resin-bound dipeptide in accordance with Fmoc methodology. All subsequent amino acid couplings followed Fmoc methodology unless otherwise specified.

The amino acid derivative introduced in the 6 position was one of: Fmoc-Cys(Trt)-OH; Fmoc-Hcy(t-butoxycarbonylethyl)-OH or Fmoc-Cys(t-butoxycarbonylpropyl)-OH. Peptide analogues where position 6 was Fmoc-Cys(Trt)-OH required coupling of Mpa(Trt)-OH to the N-terminus of the resin-bound nonapeptide residue.

The peptides synthesised using a rink amide resin support were cleaved from the resin, together with any acid labile protecting groups such as Boc, trityl and t-butyl, with TFA/TIS/$H_2O$ 95/2.5/2.5 (v/v/v) solution. Said peptides were cyclised after cleavage of the peptide from the resin. The peptides synthesised using an MBHA resin support were cleaved from the resin with HF/anisole 14/1 (v/v) solution. Said peptides were cyclised prior to cleavage of the peptide from the resin.

Cyclisation of the linear nonapeptide through disulfide (ring) formation was achieved by oxidation of linear peptides dissolved in 10% TFA (aq) with iodine. Cyclisation of the linear nonapeptide through amide bond formation was achieved by mediation with HBTU/DIPEA/DMF or PyBOP/DIPEA/DMF at a high dilution.

Peptides were purified by preparative HPLC in triethylammonium phosphate buffers (aq) and desalted with acetic acid (aq)/acetonitrile buffer system. The fractions with a purity exceeding 97% were pooled and lyophilised.

Table 1 lists the compounds prepared by the above procedure. An asterisk '*' marks the most preferred embodiments.

TABLE 1

Compounds prepared with the formula (I)

| SEQ ID No. | W | X | $R_1$ | n | $R_2$ | p | $R_3$ |
|---|---|---|---|---|---|---|---|
| 1 | $CH_2$ | S | 4-methoxyphenyl | 1 | $CH_2$—(R)—$CH(OCH_3)$—$CH_2$ | — | bond |
| 2 | $CH_2$ | S | 4-methoxyphenyl | 1 | $CH_2$—(R)—$CH(SCH_3)$—$CH_2$ | — | bond |
| 3 | $CH_2$ | S | 4-ethylphenyl | 1 | $CH_2$—(R)—$CH(OCH_3)$—$CH_2$ | — | bond |

TABLE 1-continued

Compounds prepared with the formula (I)

| SEQ ID No. | W | X | $R_1$ | n | $R_2$ | p | $R_3$ |
|---|---|---|---|---|---|---|---|
| 4 | S | $CH_2$ | 4-ethylphenyl | 1 | $CH_2$—(S)—CH(OH)—$CH_2$ | — | bond |
| 5 | $CH_2$ | S | 4-methoxyphenyl | 1 | H | 0 | H |
| 6 | $CH_2$ | S | 4-ethylphenyl | 1 | $CH_2$—(S)—CH(OH)—$CH_2$ | — | bond |
| 7 | S | S | 4-hydroxyphenyl | 1 | H | 4 | H |
| 8 | S | S | 4-hydroxyphenyl | 1 | phenyl | 2 | H |
| 9 | S | S | 4-hydroxyphenyl | 1 | 2-furyl | 1 | H |
| 10* | S | S | 4-hydroxyphenyl | 1 | 4-pyridyl | 1 | H |
| 11 | S | S | 4-hydroxyphenyl | 1 | 3,4-difluorophenyl | 1 | H |
| 12 | S | S | 4-hydroxyphenyl | 1 | 3-methylphenyl | 1 | H |
| 13 | S | S | 4-hydroxyphenyl | 1 | 2-methylphenyl | 1 | H |
| 14 | S | S | 4-hydroxyphenyl | 1 | H | 5 | H |
| 15 | S | S | 4-hydroxyphenyl | 1 | 4-methylphenyl | 2 | H |
| 16 | S | S | 4-hydroxyphenyl | 1 | 2-thienyl | 1 | H |
| 17 | S | S | 4-hydroxyphenyl | 1 | 4-pyridyl | 2 | H |
| 18* | S | S | 4-hydroxyphenyl | 1 | 2-pyridyl | 2 | H |
| 19 | S | S | 4-hydroxyphenyl | 1 | 4-fluorophenyl | 1 | H |
| 20 | S | S | 4-hydroxyphenyl | 1 | methoxy | 2 | H |
| 21 | S | S | 4-hydroxyphenyl | 1 | cyclopropyl | 1 | H |
| 22 | S | S | 4-hydroxyphenyl | 1 | 4-methoxyphenyl | 1 | H |
| 23 | S | S | 4-hydroxyphenyl | 1 | 4-methylphenyl | 1 | H |
| 24 | S | S | 4-hydroxyphenyl | 1 | 2-thienyl | 2 | H |
| 25 | S | S | 4-hydroxyphenyl | 1 | phenyl | 3 | H |
| 26 | S | S | 4-hydroxyphenyl | 1 | 2-tetrahydrofuryl | 1 | H |
| 27 | S | S | 4-hydroxyphenyl | 1 | 2-tetrahydrofuryl | 1 | H |
| 28 | S | $CH_2$ | phenyl | 1 | methoxy | 2 | H |
| 29 | $CH_2$ | S | phenyl | 1 | methoxy | 2 | H |
| 30 | $CH_2$ | S | 4-hydroxyphenyl | 1 | methoxy | 2 | H |
| 31 | S | $CH_2$ | phenyl | 1 | 2-thienyl | 1 | H |
| 32 | S | $CH_2$ | 4-hydroxyphenyl | 1 | phenyl | 1 | H |
| 33 | S | $CH_2$ | 4-hydroxyphenyl | 1 | phenyl | 2 | H |
| 34* | S | $CH_2$ | phenyl | 1 | phenyl | 1 | H |
| 35 | $CH_2$ | S | 4-hydroxyphenyl | 1 | H | 4 | H |
| 36 | S | $CH_2$ | phenyl | 1 | OH | 3 | H |
| 37 | $CH_2$ | S | phenyl | 1 | H | 3 | H |
| 38 | S | $CH_2$ | phenyl | 1 | H | 3 | H |
| 39 | $CH_2$ | S | phenyl | 1 | H | 5 | H |
| 40 | S | $CH_2$ | phenyl | 1 | H | 5 | H |
| 41 | $CH_2$ | S | phenyl | 1 | H | 4 | H |
| 42 | S | $CH_2$ | phenyl | 1 | H | 4 | H |
| 43 | $CH_2$ | S | 4-hydroxyphenyl | 1 | 3,4-difluorophenyl | 1 | H |
| 44 | S | $CH_2$ | 4-hydroxyphenyl | 1 | 3-methylphenyl | 1 | H |
| 45 | S | $CH_2$ | 4-hydroxyphenyl | 1 | 4-fluorophenyl | 1 | H |
| 46 | $CH_2$ | S | 4-hydroxyphenyl | 1 | phenyl | 1 | H |
| 47* | S | $CH_2$ | phenyl | 1 | 4-fluorophenyl | 1 | H |
| 48 | $CH_2$ | S | 4-hydroxyphenyl | 1 | 2-thienyl | 1 | H |
| 49* | $CH_2$ | S | 4-hydroxyphenyl | 1 | 4-fluorophenyl | 1 | H |
| 50 | $CH_2$ | S | 4-hydroxyphenyl | 1 | 3-methylphenyl | 1 | H |
| 51* | $CH_2$ | S | 4-hydroxyphenyl | 1 | phenyl | 2 | H |
| 52* | S | $CH_2$ | phenyl | 1 | phenyl | 2 | H |
| 53 | S | $CH_2$ | phenyl | 1 | 3-methylphenyl | 1 | H |
| 54 | $CH_2$ | S | 4-hydroxyphenyl | 1 | OH | 3 | H |

The following detailed examples are provided to further illustrate the synthesis:

In all syntheses analytical HPLC was performed on a waters 600 Liquid Chromatograph using a Vydac C18, 5 μm, 4.6×250 mm column at a flow rate of 2 ml/min. Preparative HPLC was performed on a Waters 2000 Liquid Chromatograph using a PrePak 47×300 mm cartridge at a flow rate of 100 ml/min. Final compound analysis was performed on a 1100 Agilent Liquid Chromatograph using a Vydac C18, 5 μm, 2.1×250 mm column at a flow rate of 0.3 ml/min. Mass spectra were recorded on a Finnigan MAT spectrometer.

Compound 49; carba-1-[4-FBzlGly[7]]dOT:

The amino acid derivatives used were Fmoc-Gly-OH, Fmoc-Leu-OH, Fmoc-Cys(t-butoxycarbonylpropyl)-OH, Fmoc-Asn(Trt)-OH, Fmoc-Gln(Trt)-OH, Fmoc-Ile-OH and Boc-Tyr(tBu)-OH (Peptides International). Fmoc-Cys(t-butoxycarbonylpropyl)-OH was synthesized as above.

The fully protected peptide resin was manually synthesised, starting from 1.45 g (0.87 mmol) of Rink Amide AM resin (200-400 mesh, Novabiochem). DIC/HOBt/DMF mediated single couplings with a 3-fold excess of amino acid Gly and Leu derivatives were performed. The N-(4-fluorobenzyl)glycine residue was introduced with a 4-fold excess of $BrCH_2CO_2H$/DIC/HOBt in DMF and subsequent bromine substitution with a 10-fold excess of 4-fluorobenzyl amine in DMF. DIC/DCM mediated coupling with a 4-fold excess of Fmoc-Cys(t-butoxycarbonylpropyl)-OH was performed. Subsequent DIC/HOBt/DMF mediated single couplings with a 3-fold excess of amino acid Asn, Gln, Ile and Tyr derivatives were performed. The Fmoc groups were removed with 20% piperidine in DMF. Upon completion of the solid phase synthesis, the resin was treated with a TFA/TIS/$H_2O$ 96/2.5/1.5 (v/v/v) solution (50 ml) for 1.5 h and filtered off. The filtrate was concentrated in vacuo and the crude linear peptide was precipitated with diethyl ether. The precipitate in DMF (300 ml) was added in 3 portions (3×100 ml) to a vigorously stirred solution of DIPEA (1 ml) in DMF (100 ml). HBTU (150 mg) in DMF (5 ml) was added to the reaction mixture after addition of each 100 ml portion of peptide solution; the pH of the reaction solution was maintained at pH 9 by addition of neat DIPEA, as required. The reaction was monitored by analytical HPLC. The reaction solution was concentrated in vacuo and the residue was dissolved in AcOH/$CH_3CN$/$H_2O$. The mixture was loaded onto an HPLC column and purified using a triethylammonium phosphate buffer with pH 5.2. the compound was eluted with a gradient of acetonitrile. The fractions with a purity exceeding 97% were pooled, diluted with water (2 volumes), and loaded onto a column pre-equilibrated with 2% AcOH (aq). The desired compound was eluted with a fast (3%/min) gradient of $CH_3CN$. The fractions containing the desired product were pooled and lyophilised. 434 mg (~40% yield, based on the loading of the starting resin and assuming 85% peptide content) of white amorphous powder was obtained. HPLC: Rt=19.4 min, gradient: 5% B for 0.5 min., 5→30% B in 0.5 min, 30→50% B over 20 min and 100% B for 5 min., t=40° C., solvent A 0.01% TFA (aq), solvent B 70% $CH_3CN$, 0.01% TFA (aq); Purity: 99.3%; MS (M+H$^+$): expected 1042.4, observed 1042.5.

The following is an exemplary large scale (i.e. scale-up) synthesis of Compound 49; carba-1-[4-FBzlGly$^7$]dOT:

The amino acid derivatives used were Fmoc-Gly-OH, Fmoc-Leu-OH, Fmoc-4-FBzlGly-OH, Fmoc-Cys(t-butoxycarbonylpropyl)-OH, Fmoc-Asn(Trt)-OH, Fmoc-Gln(Trt)-OH, Fmoc-Ile-OH and Boc-Tyr(tBu)-OH (Peptides International). Fmoc-4-FBzlGly-OH and Fmoc-Cys(t-butoxycarbonylpropyl)-OH were synthesized as above. The peptide was synthesised by DIC/HOBt/DMF mediated single couplings with a 3-fold excess of amino acid derivative. The remaining synthesis and characterisation of compound 49 was followed as provided above. 434 mg (~40% yield, based on the loading of the starting resin and assuming 85% peptide content) of white amorphous powder was obtained.

Compound 10; [4-PicGly$^7$]dOT:

The amino acid derivatives used were Fmoc-Gly-OH, Fmoc-Leu-OH, Fmoc-Cys(Trt)-OH, Fmoc-Asn(Trt)-OH, Fmoc-Gln(Trt)-OH, Fmoc-Ile-OH, Fmoc-Tyr(tBu)-OH and Mpa(Trt)-OH (Peptides International). The fully protected peptide resin was manually synthesized, starting from 1.33 g (0.65 mmol) of Rink AM resin (200-400 mesh, Novabiochem). DIC/HOBt/DMF mediated single couplings with a 3-fold excess of amino acid Gly and Leu derivatives were performed. The N-(4-picolyl)glycine residue was introduced with a 4-fold excess of $BrCH_2CO_2H$/DIC/HOBt in DMF and subsequent bromine substitution with a 10-fold excess of 4-picolyl amine in DMF. DIC/DCM mediated coupling with a 4-fold excess of Fmoc-Cys(Trt)-OH and DIC/HOBt/DMF mediated single couplings with a 3-fold excess of amino acid Asn, Gln, Ile, Tyr and Mpa derivatives were performed. The Fmoc groups were removed with 20% piperidine in DMF. Upon completion of the solid phase synthesis, the resin was treated with TFA/TIS/$H_2O$ 96/2/2 (v/v/v) solution (50 ml) for 1.5 h and filtered off. The filtrate was concentrated in vacuo and the crude linear peptide was precipitated with diethyl ether. The precipitate was dissolved in neat TFA (50 ml), poured onto a magnetically stirred 5% aqueous acetonitrile (600 ml) solution and the peptide was oxidised by adding 0.1 M $I_2$ in methanol until yellow colour persisted. Excess of iodine was reduced with solid ascorbic acid (Sigma-Aldrich) and the pH of the solution was adjusted to about 4 by adding concentrated ammonia (aq). The mixture was loaded onto an HPLC column and purified using a triethylammonium phosphate buffer with pH 5.2. The compound was eluted with a gradient of acetonitrile. The fractions with a purity exceeding 97% were pooled, diluted with water (2 volumes), and loaded onto a column pre-equilibrated with 2% AcOH (aq). The desired compound was eluted with a fast (3%/min) gradient of acetonitrile. The fractions containing the desired product were pooled and lyophilised. 348.7 mg (~44% yield, based on the loading of the starting resin and assuming 85% peptide content) of white amorphous powder was obtained. HPLC: Rt=21.7 min, gradient: 5% B for 0.5 min., 5→10% B in 0.5 min, 10→30% B over 20 min and 100% B for 5 min., t=40° C., solvent A 0.01% TFA (aq), solvent B 70% $CH_3CN$, 0.01% TFA (aq); Purity: 99.9%; MS (M+H$^+$): expected 1043.4, observed 1043.4.

Compound 29; carba-6-[Phe$^2$, MeOEtGly$^7$]dOT:

The amino acid derivatives used were Boc-Gly-OH and Boc-Leu-OH (Bachem), Fmoc-Hcy(t-butoxycarbonylethyl)-OH, Fmoc-Asn(Trt)-OH, Fmoc-Gln(Trt)-OH, Fmoc-Ile-OH and Boc-Phe-OH (Peptides International). Fmoc-Hcy(t-butoxycarbonylethyl)-OH was synthesized as above.

The fully protected peptide resin was manually synthesized starting from 1.33 g of MBHA resin (0.94 mmol, Novabiochem). The resin was neutralized with 10% TEA in DCM. DIC/DCM mediated single couplings with a 1.7-fold excess of amino acids Boc-Gly-OH and Boc-Leu-OH were performed. The N-(2-methoxyethyl)glycine residue was introduced with a 3.6-fold excess of $BrCH_2CO_2H$/DIC/HOBt in DMF and subsequent substitution of the bromine with a 7-fold excess of 2-methoxyethyl amine and a 4-fold excess of DIPEA in DMF (10 ml); the reaction was stirred for 5 h. DIC/DCM mediated single coupling with a 4-fold excess of Fmoc-Hcy(t-butoxycarbonylethyl)-OH and DIC/HOBt/DMF mediated single couplings with a 3-fold excess of amino acid Asn and Gln derivatives were performed. The two final single couplings with Fmoc-Ile-OH and Boc-Phe-OH were performed with DIC/DCM to provide the desired protected resin-bound linear peptide. The Fmoc groups were removed with 20% piperidine in DMF. The resin was treated with TFA/$H_2O$/TIS 95/3/2 (v/v/v) for 2 h to remove the trityl, Boc, and t-butyl groups. BOP (4 eq) and DIPEA (10 eq) were added to a stirred suspension of the resin in DMF (10 mL); after 2 h PyBOP (2 eq) and DIPEA (5 eq) were added. The peptide was cleaved from the resin by using 70 ml of anhydrous HF containing 5 ml of anisole at 0° C. for 90 mins. The HF was removed in vacuo and the crude linear peptide was washed with diethyl; ether (300 ml). The peptide was dissolved in AcOH/$CH_3CN$/$H_2O$ 1/2/7 (v/v/v) (400 ml). The resulting mixture was loaded directly onto an HPLC column and purified using triethylammonium phosphate buffer at pH 2.3. The compound was eluted with an acetonitrile gradient. The fractions with a purity exceeding 97% were pooled, diluted with water (2 volumes), and loaded onto a column pre-equilibrated with 2% acetic acid (aq). The desired compound was eluted with a 1% AcOH/$CH_3CN$ gradient. The fractions containing the desired product were pooled and lyophilised.

292.7 mg (~27% yield, based on the loading of the starting resin and assuming 85% peptide content) of white amorphous powder was obtained. HPLC: Rt=16.7 min, gradient: 5% B for 0.5 min., 5→30% B in 0.5 min, 30→50% B over 20 min and 100% B for 5 min., t=40° C., solvent A 0.01% TFA (aq), solvent B 70% $CH_3CN$, 0.01% TFA (aq); Purity: 100.0%; MS. (M+H$^+$): expected 976.5, observed 976.3.

The other compounds were prepared by analogous variation of these synthetic procedures.

EXPERIMENTAL

Biological Testing

In Vitro Receptor Assays:

Agonist activity of compounds on the hOT receptor was determined in a transcriptional reporter gene assay by transiently transfecting a hOT receptor expression DNA into a Chinese Hamster Ovary (CHO) cell line in concert with a reporter DNA containing intracellular calcium responsive promoter elements regulating expression of firefly luciferase. See Boss, V., Talpade, D. J., Murphy, T. J. *J. Biol. Chem.* 1996, May 3; 271(18), 10429-10432 for further guidance on this assay. Cells were exposed to serial dilutions of compounds diluted 10-fold per dose for 5 h, followed by lysis of cells, determination of luciferase activity, and determination of compound efficacies and $EC_{50}$ values through non-linear regression. Oxytocin (OT) was used as an internal control in each experiment, and compounds were tested in at least three independent experiments. To determine selectivity, compounds were further tested in luciferase-based transcriptional reporter gene assays expressing the human vasopressin ($hV_2$) receptor.

For further comparative purposes carbetocin was also used as a reference compound.

The results of the in vivo assays are depicted in table 2 infra. The $EC_{50}$ value given is the geometric mean expressed in nanomol/l (nM). Selectivity values are given as $EC_{50}$ ratios.

TABLE 2

Results of biological testing

| Compound Tested | $EC_{50}$ hOT receptor | $EC_{50}$ hV$_2$ receptor | Selectivity hV$_2$/hOT |
|---|---|---|---|
| 1 | 0.980 | 688.22 | 702 |
| 2 | 0.817 | 671.12 | 822 |
| 3 | 0.207 | 446.76 | 2158 |
| 4 | 0.033 | 17.70 | 544 |
| 5 | 0.370 | 448.67 | 1211 |
| 6 | 0.064 | 39.95 | 629 |
| 7 | 0.062 | 34.78 | 558 |
| 8 | 0.116 | 65.55 | 565 |
| 9 | 0.114 | 61.79 | 544 |
| 10 | 0.464 | 384.04 | 828 |
| 11 | 0.026 | 58.54 | 2217 |
| 12 | 0.011 | 29.78 | 2607 |
| 13 | 0.121 | 67.81 | 562 |
| 14 | 0.005 | 77.11 | 15124 |
| 15 | 0.040 | 101.77 | 2533 |
| 16 | 0.009 | 57.29 | 6067 |
| 17 | 0.023 | 47.27 | 2014 |
| 18 | 0.115 | 180.32 | 1561 |
| 19 | 0.012 | 82.03 | 6607 |
| 20 | 0.030 | 80.29 | 2659 |
| 21 | 0.006 | 9.87 | 1729 |
| 22 | 0.063 | 77.83 | 1245 |
| 23 | 0.148 | 83.55 | 565 |
| 24 | 0.016 | 86.10 | 5469 |
| 25 | 0.058 | 159.44 | 2736 |
| 26 | 0.072 | 226.14 | 3160 |
| 27 | 0.189 | 238.02 | 1259 |
| 28 | 0.847 | 1264.33 | 1493 |
| 29 | 0.957 | 1100.45 | 1149 |
| 30 | 0.109 | 69.68 | 639 |
| 31 | 0.297 | 760.80 | 2564 |
| 32 | 0.051 | 35.83 | 705 |
| 33 | 0.046 | 100.71 | 2203 |
| 34 | 0.405 | 718.38 | 1774 |
| 35 | 0.122 | 72.66 | 597 |
| 36 | 0.859 | 2551.62 | 2970 |
| 37 | 0.228 | 441.72 | 1941 |
| 38 | 0.271 | 227.03 | 839 |
| 39 | 0.254 | 2058.97 | 8115 |
| 40 | 0.069 | 1024.67 | 14945 |
| 41 | 0.227 | 1999.84 | 8793 |
| 42 | 0.086 | 1192.93 | 13901 |
| 43 | 0.104 | 123.61 | 1187 |
| 44 | 0.023 | 55.14 | 2404 |
| 45 | 0.036 | 140.24 | 3914 |
| 46 | 0.039 | 140.36 | 3632 |
| 47 | 0.228 | 1415.28 | 6221 |
| 48 | 0.089 | 253.03 | 2854 |
| 49 | 0.08 | 328.57 | 4293 |
| 50 | 0.077 | 212.57 | 2761 |
| 51 | 0.045 | 161.91 | 3614 |
| 52 | 0.779 | 3005.36 | 3860 |
| 53 | 0.562 | 1613.76 | 2870 |
| 54 | 0.013 | 496.61 | 37735 |
| oxytocin | 2.34 | 7.33 | 3 |
| carbetocin | 0.70 | 171.98 | 244 |

The foregoing results indicate that the Example compounds are within the scope of the invention and may for instance be useful in the safe and efficacious treatment of human beings in order to induce labour, control uterine atony, promote and maintain lactation etc.

The scope of the present invention is further defined in the following claims.

The invention claimed is:

1. A compound having the formula (I):

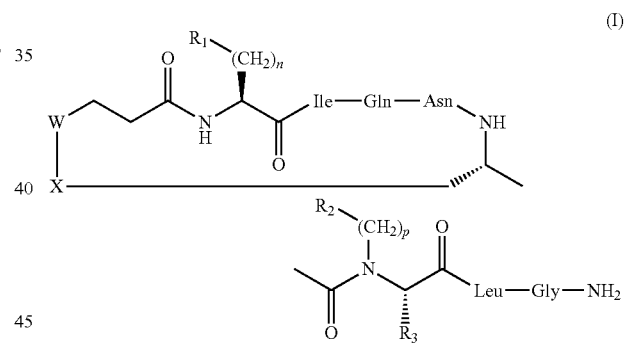

wherein:
n is selected from 0, 1 and 2;
p is selected from 0, 1, 2, 3, 4, 5 and 6;
$R_1$ is selected from phenyl optionally substituted with at least one of the substituents selected from the group consisting of OH, F, Cl, and Br; $C_{1-6}$ straight or $C_{4-8}$ branched chain alkyl optionally having at least one hydroxyl substituent; or $C_{1-6}$ straight or $C_{4-8}$ branched chain alkoxy optionally having at least one hydroxyl substituent;
$R_2$ is selected from H, methoxy, $C_{4-8}$ branched chain alkyl optionally having at least one hydroxyl substituent, $C_{2-6}$ straight chain alkyl having at least one hydroxyl substituent, substituted or unsubstituted cycloalkyl, substituted or unsubstituted phenyl, and substituted or unsubstituted 5- and 6-membered heteroaromatic ring systems;
$R_3$ is H; and
W and X are each independently selected from $CH_2$ and S, provided that W and X are not both $CH_2$;

with the proviso that when $R_2$ is H, p is 0 or 1, n is 1 and W and X are both S, then $R_1$ is not 4-hydroxyphenyl; and solvates and pharmaceutically acceptable salts thereof.

2. A compound according to claim 1, wherein the heteroaromatic ring systems are optionally substituted with at least one alkyl, O-alkyl, OH, F, Cl or Br substituent.

3. A compound according to claim 1, wherein n is 1.

4. A compound according to claim 1, wherein p is selected from 0, 1, 2, 3, 4 and 5.

5. A compound according to claim 1, wherein $R_1$ is selected from the group consisting of phenyl, 4-hydroxyphenyl, 4-methoxyphenyl and 4-ethylphenyl.

6. A compound according to claim 1, wherein $R_2$ is selected from the group consisting of cyclopropyl, 2-hydroxyethyl, methoxy, phenyl, 2-methylphenyl, 3-methylphenyl, 4-methylphenyl, 4-methoxylphenyl, 4-fluorophenyl, 3,4-difluorophenyl, 2-thienyl, 2-tetrahydrofuryl, 2-furyl, 2-pyridyl and 4-pyridyl.

7. A compound according to claim 1, wherein W is $CH_2$ and X is S.

8. A compound according to claim 1, wherein W is S and X is $CH_2$.

9. A compound according to claim 1, wherein W and X are both S.

10. A compound according to claim 1 wherein $R_2$ is selected from unsubstituted or substituted cycloalkyl, substituted or unsubstituted phenyl, and substituted or unsubstituted 5- and 6-membered hetero aromatic ring systems.

11. A compound according to claim 1, wherein the compound is selected from a group consisting of:

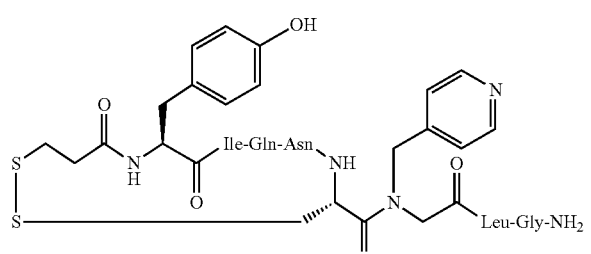

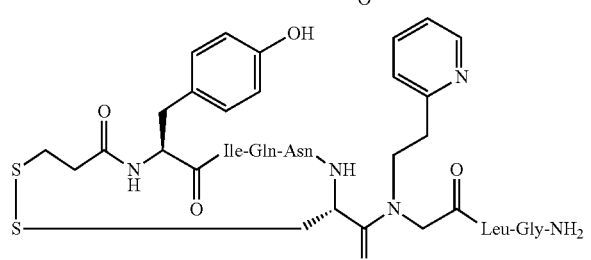

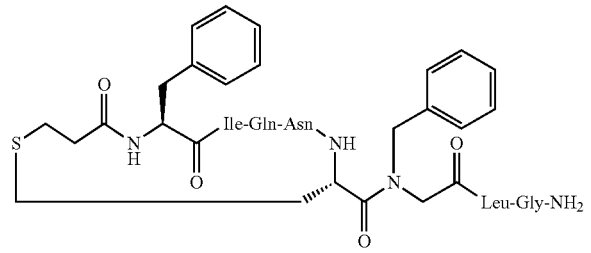

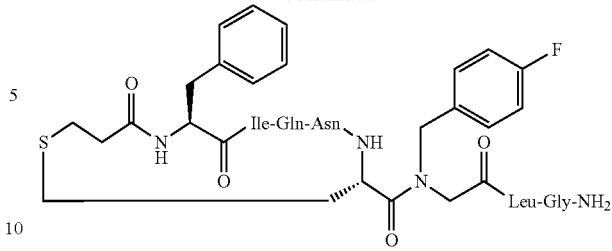

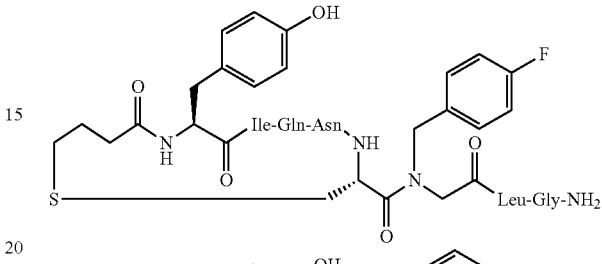

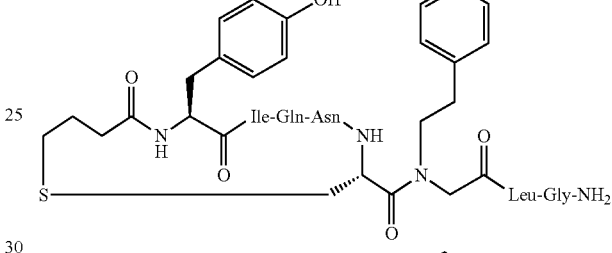

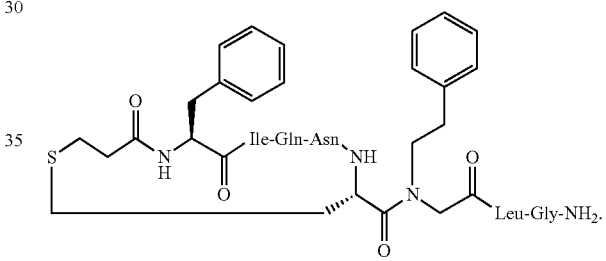

12. A pharmaceutical composition comprising a compound according to claim 1 and a pharmaceutically acceptable adjuvant, diluent or carrier.

13. A method for treatment of a condition selected from the group consisting of a compromised lactation condition, labour induction impairment, a uterine atony condition, inflammation, pain, male and female sexual dysfunction, irritable bowel syndrome (IBS), constipation, gastrointestinal obstruction, autism, stress, anxiety, depression, anxiety disorder, surgical blood loss, post-partum haemorrhage, wound healing, infection, mastitis, placenta delivery impairment, and osteoporosis, wherein said method comprises administering to an animal in need thereof a therapeutically effective amount of a compound according to claim 1.

14. The method of claim 13, wherein the condition is abdominal pain or back pain.

15. The method of claim 13, wherein the animal is a human.

16. The compound of claim 1, wherein
n is selected from 1 and 2;
p is selected from 1, 2, 3, 4, 5 and 6;
$R_1$ is selected from phenyl optionally substituted with one of the substituents selected from the group consisting of OH, F, Cl, Br, $C_{3-6}$ straight or $C_{4-8}$ branched chain alkyl optionally having at least one hydroxyl substituent, or $C_{3-6}$ straight or $C_{4-8}$ branched chain alkoxy optionally having at least one hydroxyl substituent; and R₂ is selected from H, methoxy, $C_{4-8}$ branched chain alkyl optionally having at least one hydroxyl substituent, $C_{3-6}$ straight chain alkyl having at least one hydroxyl substituent, phenyl, 3-methylphenyl, 4-methylphenyl, 4-fluorophenyl, and 2-thienyl.

17. The compound of claim 16, wherein n is 1.

18. The compound of claim 16, wherein p is 1, 2, 3, 4, or 5.

19. The compound of claim 16, wherein R₁ is phenyl or 4-hydroxyphenyl.

20. The compound of claim 16, wherein R₂ is methoxy, 2-hydroxyethyl, phenyl, 3-methylphenyl, 4-methylphenyl, 4-fluorophenyl, or 2-thienyl.

21. The compound of claim 1, wherein the compound is selected from the group consisting of:

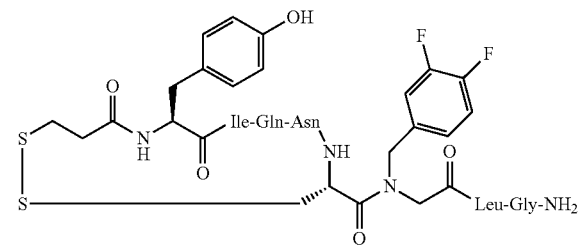
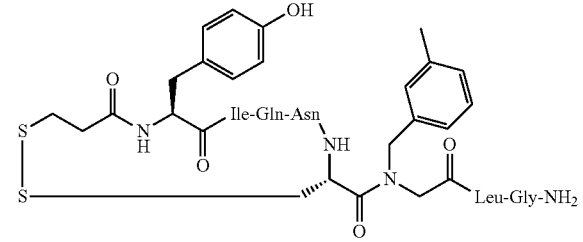
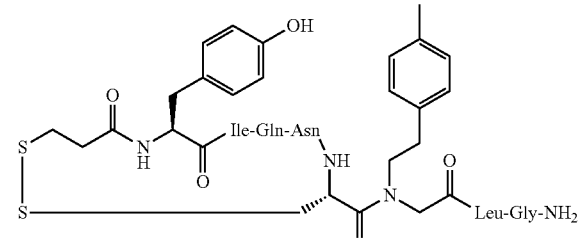
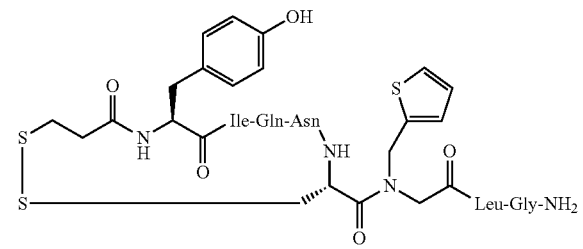
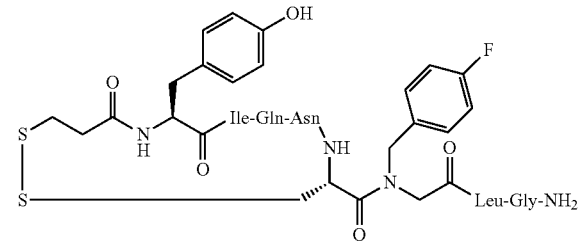
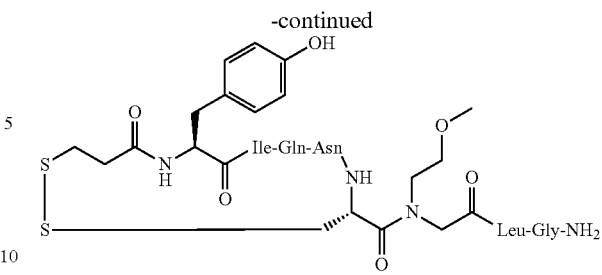
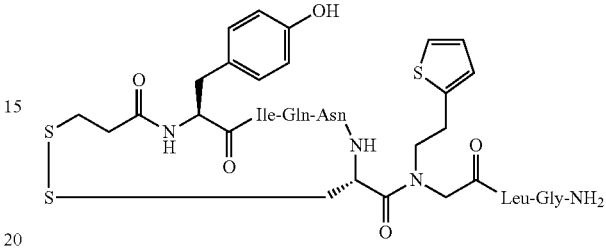
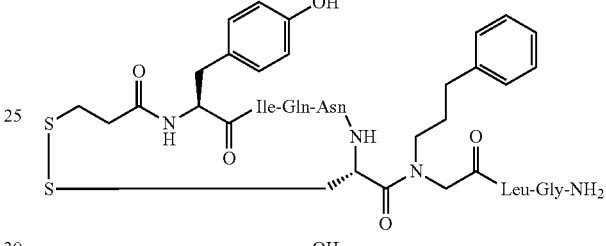
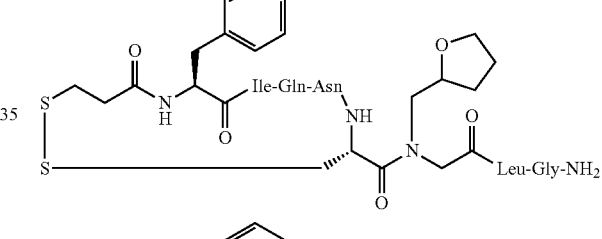
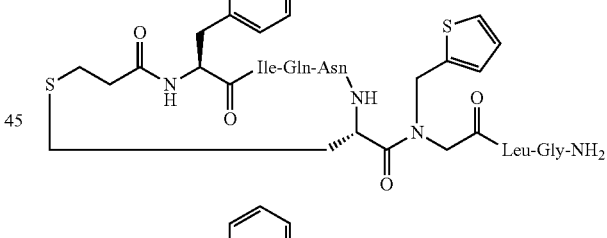
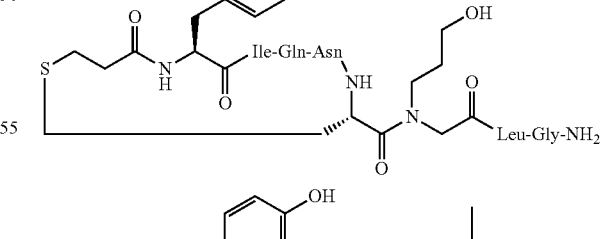
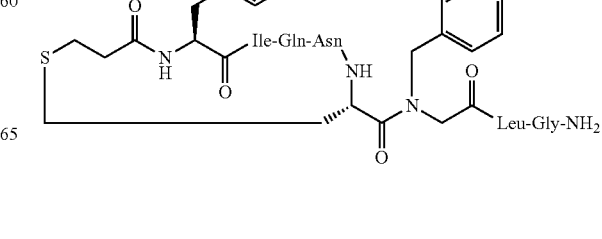

-continued
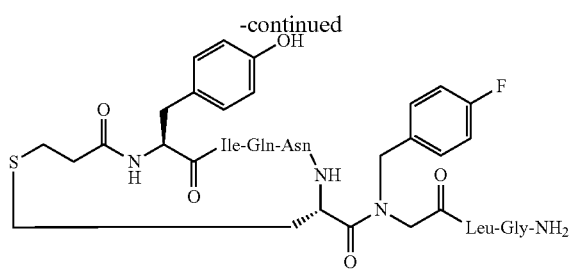
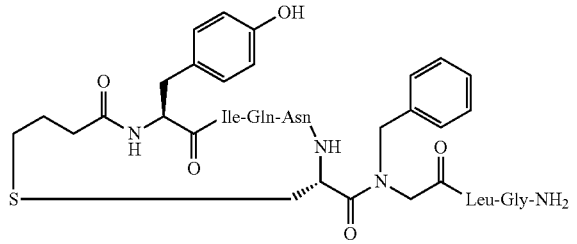
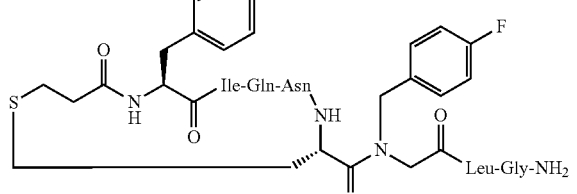
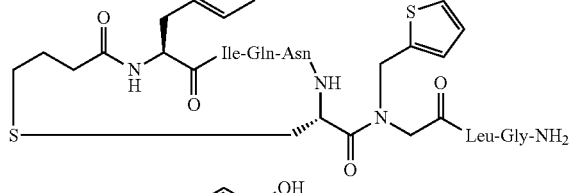
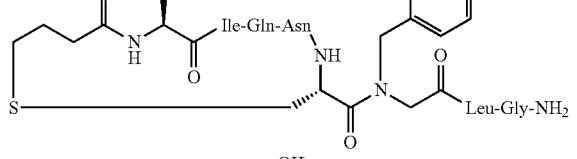
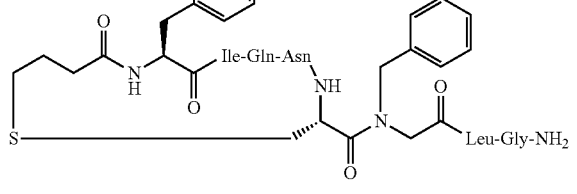
-continued
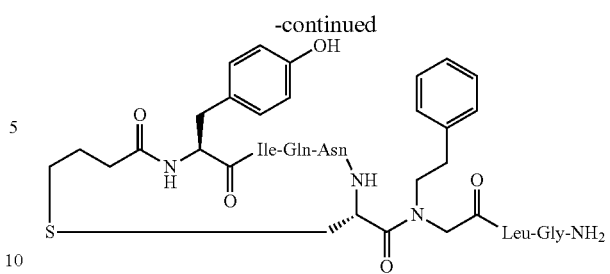
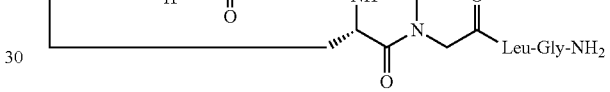
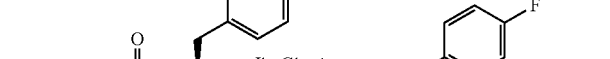
22. The compound of claim 1, wherein the compound is:
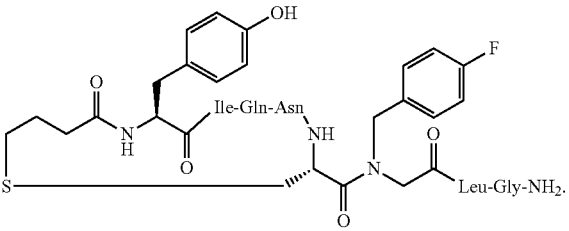
* * * * *

UNITED STATES PATENT AND TRADEMARK OFFICE
CERTIFICATE OF CORRECTION

PATENT NO. : 8,673,841 B2  
APPLICATION NO. : 12/933858  
DATED : March 18, 2014  
INVENTOR(S) : Alagarsamy et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 382 days.

Signed and Sealed this
Twenty-first Day of July, 2015

Michelle K. Lee
*Director of the United States Patent and Trademark Office*